United States Patent [19]

Misra

[11] Patent Number: 5,126,370
[45] Date of Patent: Jun. 30, 1992

[54] ANTI-THROMBOTIC HETEROCYCLIC AMIDO PROSTAGLANDIN ANALOGS

[75] Inventor: Raj N. Misra, Hopewell, N.J.

[73] Assignee: E. R. Squibb & Sons, Inc., Princeton, N.J.

[21] Appl. No.: 632,560

[22] Filed: Dec. 24, 1990

[51] Int. Cl.⁵ .................. A61K 31/34; C07D 307/00
[52] U.S. Cl. ................... 514/469; 549/463; 548/236; 546/196
[58] Field of Search ............ 549/463; 514/469

[56] References Cited

U.S. PATENT DOCUMENTS

| | | | |
|---|---|---|---|
| 4,416,896 | 11/1983 | Nakane et al. | 549/463 |
| 4,418,076 | 11/1983 | Nakane et al. | 549/463 |
| 4,463,015 | 7/1984 | Haslanger et al. | 549/463 |
| 4,474,804 | 10/1984 | Das et al. | 549/463 |
| 4,522,949 | 6/1985 | Das et al. | 549/463 |
| 4,536,513 | 8/1985 | Das et al. | 549/463 |
| 4,663,336 | 5/1987 | Nakane et al. | 549/463 |
| 4,663,337 | 5/1987 | Das et al. | 549/463 |

OTHER PUBLICATIONS

As Belo Bioorg Chem, 04.03.81-SU278256 (23.11.87) C07c-177 C07d-261/06.
Chem. Abs.-CA Selects: Prostaglandins Issue 12, 1988 108:198903m, Kuz'mitskii, B. B. et al.
Chem. Abs.-CA Selects: Prostaglandins, Issue 12, 1988, 108:204363d, Lakhvich, F. A. et al.

Primary Examiner—Bernard Dentz
Attorney, Agent, or Firm—Timothy J. Gaul

[57] ABSTRACT

Prostaglandin analogs useful in treating thrombotic and vasospastic disease having the structural formula

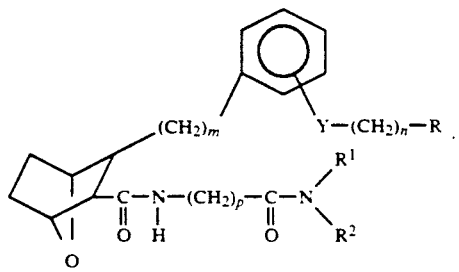

wherein:
m is 1, 2 or 3;
n is 1, 2 or 3, except that n is 0 when Y is vinylene;
p is 1, 2 or 3;
R is $CO_2R'$, $CH_2OH$, $CONHSO_2R^3$, $CONHR^4$, or $-CH_2$-5-tetrazolyl;
R' is hydrogen, alkyl, or alkali metal;
Y is $-O-$, a single bond or vinylene, except that Y cannot be $-O-$ when n is 0;
and the remaining symbols are as defined in the specification.

24 Claims, No Drawings

ANTI-THROMBOTIC HETEROCYCLIC AMIDO PROSTAGLANDIN ANALOGS

FIELD OF THE INVENTION

This invention relates to prostaglandin analogs useful as thromboxane $A_2$ receptor antagonists.

BRIEF DESCRIPTION OF THE INVENTION

A compound of the formula

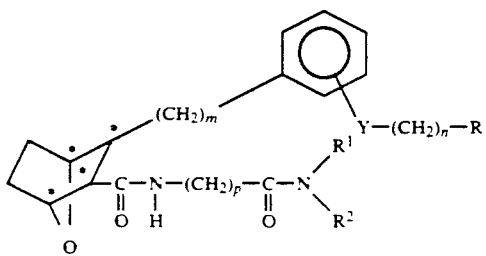

is a thromboxane $A_2$ ($TXA_2$) receptor antagonist or a combined thromboxane $A_2$ receptor antagonist/thromboxane synthetase inhibitor. Compound I is useful, for example, in treating thrombotic or vasospastic disease. In compound I and throughout this specification, the symbols above are defined as follows:

m is 1, 2, or 3;

n is 1, 2 or 3, except that n is O when Y is vinylene;

p is 1, 2 or 3;

R is $CO_2R'$, $CH_2OH$, $CONHSO_2R^3$, $CONHR^4$, or $-CH_2$-5-tetrazolyl;

R' is hydrogen, alkyl, or alkali metal;

Y is $-O-$, a single bond or vinylene, except that Y cannot be $-O-$ when n is 0;

$R^1$ is hydrogen, alkyl, alkenyl, alkynyl, aralkyl, aryl, cycloalkyl, cycloalkylalkyl, cycloheteroalkyl, cycloheteroalkylalkyl, heteroaryl or heteroarylalkyl, or amide

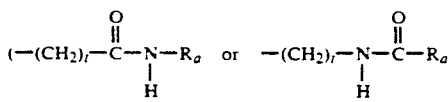

wherein t is 1 to 12 and $R_a$ is alkyl, aryl, cycloalkyl, or cycloalkylalkyl), each of $R^1$ being unsubstituted or optionally substituted with alkyl, aryl, cycloalkyl, or cycloalkylalkyl;

$R^2$ is hydrogen, alkyl, aryl, or aralkyl; or $R^1$ and $R_2$ together with the nitrogen to which they are linked may form a 5- to 8-membered ring;

$R_3$ is alkyl, aryl or aralkyl; and $R_4$ is hydrogen, alkyl, aryl, aryl or aralkyl.

Thus, the compounds of the invention include the following types of compounds, which are preferred:

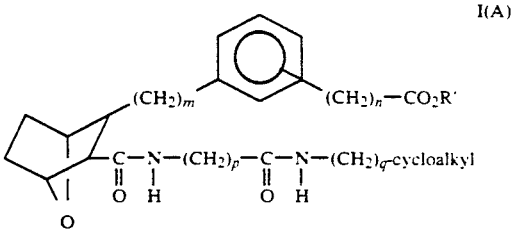

wherein q is an integer from 1 to 7. Most preferred are those compounds wherein R' is hydrogen, m is 1, n is 1 or 2, p is 1, q is 4, the cycloalkyl group is cyclohexyl, and the substitution on the aromatic ring is ortho.

DETAILED DESCRIPTION OF THE INVENTION

Definition of Terms

The term "alkyl" includes both straight and branched chain radicals of up to 12 carbons, preferably 1 to 4 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof and the like, which may be substituted with one or two trifluoromethyl, halo or hydroxyl groups.

The term "cycloalkyl" includes saturated cyclic hydrocarbon groups containing 3 to 12 carbons, preferably 3 to 8 carbons, which include cyclopropyl, cyclobutyl, cyclopentyl, cyclohexyl, cycloheptyl, cyclooctyl, cyclodecyl and cyclododecyl.

The term "aryl" or "Ar" refers to monocyclic or bicyclic aromatic groups containing from 6 to 10 carbons in the ring portion, such as phenyl and naphthyl, which may include 1 or 2 substituents on either the phenyl or naphthyl such as alkyl, trifluoromethyl, halogen (Cl, Br, I or F), alkoxy, arylalkoxy, hydroxy, alkylthio, alkylsulfinyl, alkylsulfonyl, phenylthio, phenylsulfinyl and/or phenylsulfonyl.

The term "aralkyl" refers to alkyl groups as discussed above having an aryl substituent, such as benzyl.

The terms "alkoxy" and "aralkoxy" refer to the above alkyl and aralkyl groups linked to an oxygen atom.

The term "halogen" or "halo" refers to chlorine, bromine, fluorine or iodine, with chlorine being preferred.

The term "alkenyl" as employed herein with respect to the $R^1$ substituent includes a carbon chain of up to 12 carbons, preferably 3 to 10 carbons, having at least one double bond, which will be separated from "N" by at least one saturated carbon moiety such as $-(CH_2)_q-$ wherein q can be 1 to 14, such as 2-propenyl, 2-butenyl, 3-butenyl, 2-pentenyl, 4-pentenyl and the like, and may include a halogen substituent such as I, Cl, or F.

The term "alkynyl" as employed herein with respect to the $R^1$ substituent includes a carbon chain of up to 16 carbons, preferably 3 to 10 carbons, having at least one triple bond, which will be separated from "N" by at least one saturated carbon moiety such as $-(CH_2)_q-$ wherein q can be 1 to 14, such as 2-propynyl, 2-butynyl, 3-butynyl and the like.

The term "cycloheteroalkyl" as used herein as an $R^1$ substituent refers to 5-, 6- or 7-membered saturated rings that include 1 or 2 heteroatoms such as nitrogen, oxygen and/or sulfur, and which are linked to the "N" of the

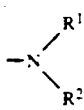

group through a carbon atom either beta or gamma to a heteroatom, such as

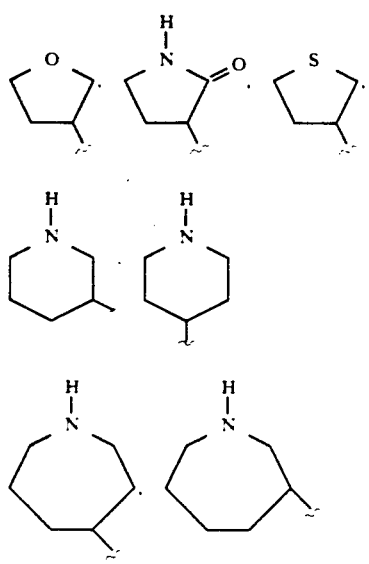

and the like.

The term "heteroaryl" or "heteroaromatic" as an $R^1$ substituent refers to 5- or 6-membered aromatic rings that include 1 or 2 heteroatoms such as nitrogen, oxygen or sulfur, which are not directly linked through a heteroatom to the "N" of the

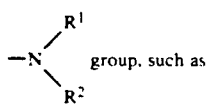 group, such as

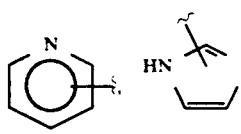

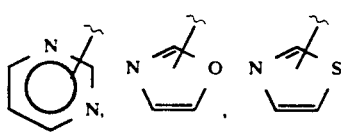

and the like.

The term "cycloheteroalkylalkyl" as used herein with respect to $R^1$ refers to 5-, 6- or 7-membered saturated rings that include 1 or 2 heteroatoms such as nitrogen, oxygen or sulfur, and are linked to the "N" of the

group through a $(CH_2)_x$ chain wherein x is 1 to 12, preferably 1 to 8, such as

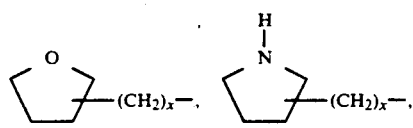

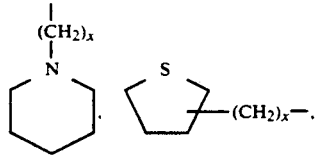

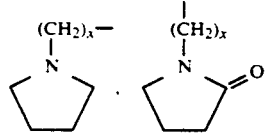

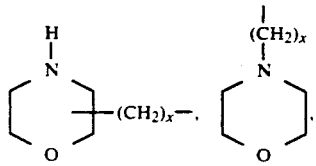

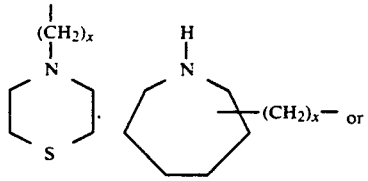

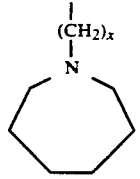

and the like.

The term "heteroarylalkyl" as used herein with respect to $R^1$ refers to 5-, 6- or 7-membered aromatic rings that include 1 to 4 nitrogen and/or 1 or 2 oxygen or sulfur atoms, and is linked to the "N" of the

group through a $-(CH_2)_x-$ chain where x is 1 to 12, preferably 1 to 8, such as

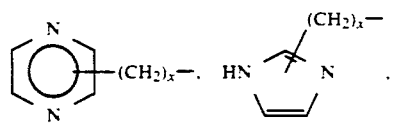

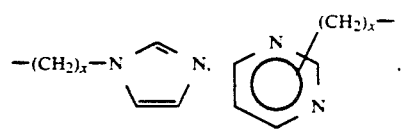

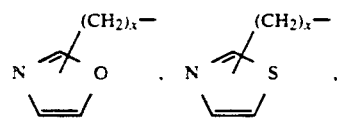

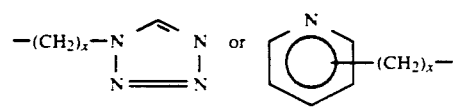

and the like.

Processes of Preparation

Compounds of the invention wherein Y is a single bond are prepared starting with bromophenylalkyl alcohol A

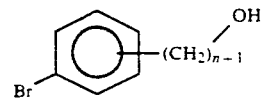   A wherein n is 1, 2, 3 or 4. Compound A is treated with a protecting compound (e.g., t-butylchlorodiphenylsilane) in the presence of an amine base (e.g., triethylamine) and an inert solvent, employing conventional procedures, to form the protected bromophenylalkyl compound B

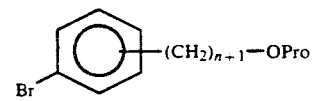   B wherein Pro represents a protecting group. Examples of protecting compounds suitable for use herein in reacting with bromophenalkyl alcohol A include but are not limited to

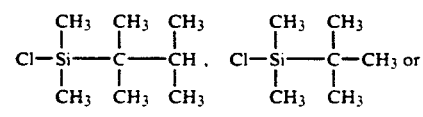

-continued

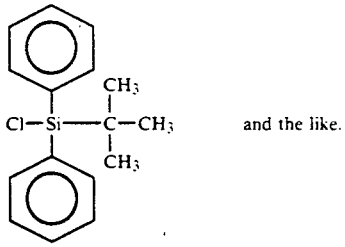   and the like.

(t-butylchlorodiphenylsilane)

The protected compound B then undergoes a metal-halogen exchange reaction by treatment with, for example, t-C$_4$H$_9$Li or n-C$_4$H$_9$Li in the presence of diethyl ether or tetrahydrofuran (THF) at about −100° to, about 0° C., or is preferably subjected to a Grignard reaction by treatment with magnesium in the presence of an inert organic solvent (e.g., THF or diethyl ether) and then is condensed with (exo)octahydro-5,8-epoxy-1H-benzopyran-3-ol or (exo)octahydro-4,7-epoxyisobenzofuran-1-ol (prepared as described in U.S. Pat. No. 4,143,054 or in Patel et al., "(exo,exo)-7-oxabicyclo[2.2.1]heptane-2,3-dimethanol, monoacyl ester, diacyl ester and enzymatic hydrolysis, thereof", U.S. Ser. No. 629,780, filed Dec. 18, 1990) of the structure C

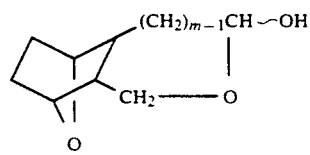   C employing a molar ratio of C:B from about 1:2 to about 1:4, in the presence of an inert organic solvent such as THF at about −78° to about 25° C. to form the condensed 7-oxabicycloheptane compound

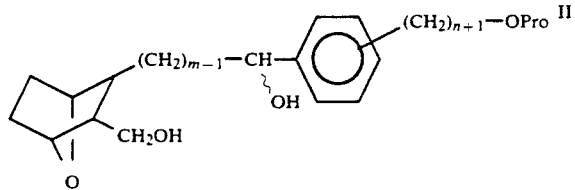   II

The condensed compound II is then subjected to hydrogenolysis by treatment with hydrogen in the presence of a catalyst (e.g., palladium hydroxide on charcoal) in acetic acid or an inert organic solvent (e.g., ethyl acetate) to form the alcohol

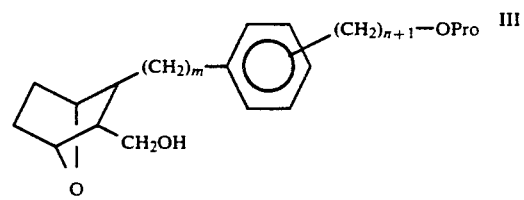   III

When the protecting group (Pro) in alcohol III is thexyldimethylsilyl or t-butyldimethylsilyl, alcohol III may be reacted with an acetylating agent (e.g., acetic anhydride) in the presence of pyridine and dimethylaminopyridine (DMAP) to form

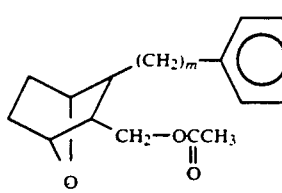

Acetylated compound IV is then reacted with Jones reagent (see Fieser and Fieser, Reagents in Organic Synthesis, Vol. 1, p. 242) at about −10 to 10° C. in acetone to form an acetate-acid

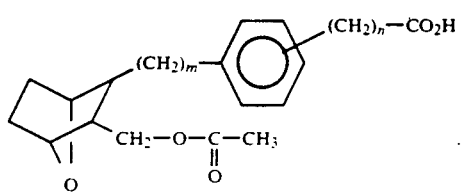

The acetate-acid V is reacted with an aqueous alkali metal hydroxide in tetrahydrofuran or excess methyllithium to form an alcohol-acid

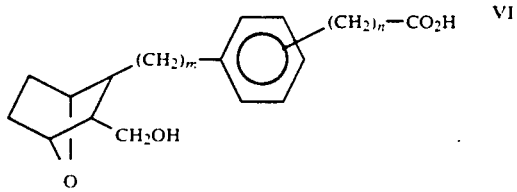

Alcohol-acid VI is then esterified with an acidic alcohol (e.g., HCl/CH₂OH) at about −10 to 10° C. to form an alcohol ester

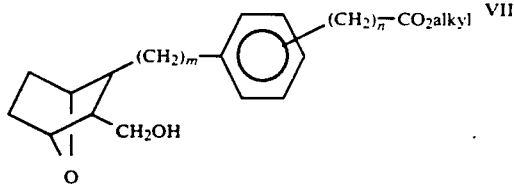

Alcohol-ester VII is oxidized with Jones reagent at about −10 to 10° C. in acetone to form an acid-ester

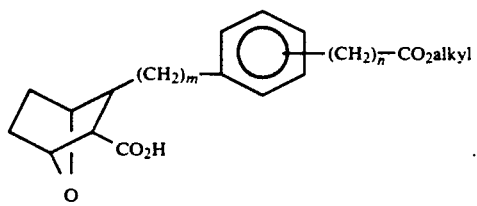

Acid VIII undergoes a coupling reaction by treatment with amine salt

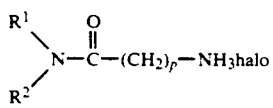

in an organic solvent such as dimethylformamide (DMF) at about −10 to 10° C. in the presence of dicyclohexylcarbodiimide (DCC) or 1-(3-dimethylaminopropyl)-3-ethylcarbodiimide hydrochloride (WSC) and 1-hydroxybenzotriazole (HOBT) and triethylamine under an inert atmosphere such as argon employing a molar of about 1.2:1 to 1:1 acid:D to form compound I wherein R is CO₂R' and R' is alkyl. It should be appreciated that when the R¹ residue in D contains a basic nitrogen functionality, it must be used in a protected form and then deprotected according to conventional procedures to form compound I wherein R is CO₂R' and R' is alkyl.

Compounds of the invention wherein Y is O may be prepared as follows.

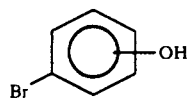

Bromophenol is treated with bromomethyl methyl ether to form the compound

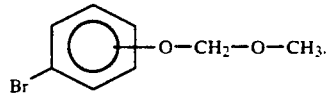

Compound E is metallated (using a procedure similar to that set out above with respect to metal-halogen exchange of B using n-butyllithium in THF) and condensed with hemiacetal C to form the condensed 7-oxabicycloheptane compound

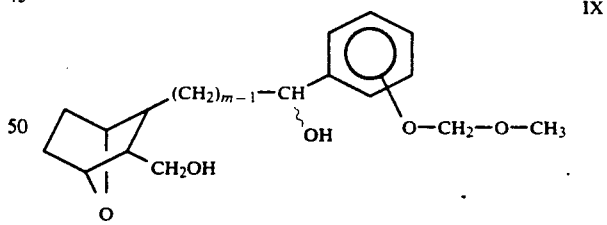

The condensed compound IX is then subjected to hydrogenolysis by treatment with hydrogen in the presence of a catalyst such as palladium on charcoal in acetic acid to form the alcohol

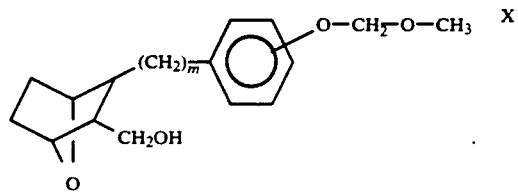

Compound X is deprotected by treatment with, for example, a solution of methanol and aqueous hydrochloric acid to form the deprotected alcohol

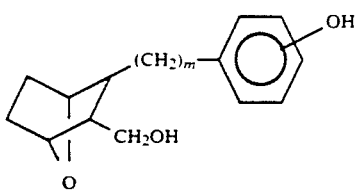

XI

The alcohol XI is then deprotonated in tetrahydrofuran with a molar equivalent of sodium hydride or one to four equivalents of a carbonate base such as potassium carbonate. The resulting phenoxide solution is alkylated by treating with a haloalkanoic acid ester F

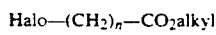

Halo—(CH$_2$)$_n$—CO$_2$alkyl        F employing a molar ratio of F:XI of about 1:1 to 3:1 in the presence of an inert organic solvent (e.g., THF, dimethylformamide, or dimethoxyethane) to form ester

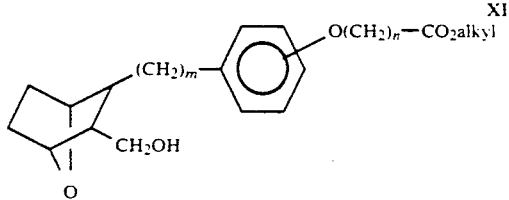

XII

Alcohol ester XII is treated as described above for compounds VII→VIII→I to form compound I wherein Y is —O—.

Compounds of formula I wherein Y is —CH=CH— may be prepared starting with alcohol A wherein n is 2, which may be prepared by subjecting the aldehyde

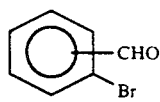

G to a Wittig reaction with (C$_6$H$_5$)$_3$PCHCO$_2$CH$_3$ to form the ester

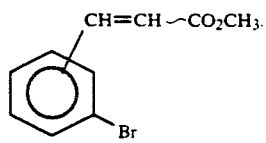

H

Ester H undergoes a double bond reduction by treatment with hydrogen in the presence of rhodium on alumina catalyst in the presence of methanol to form ester

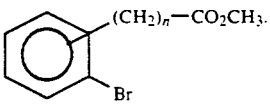

H$^1$

Ester H$^1$ is then reduced by treatment with diisobutylaluminum hydride in the presence of toluene solvent to form alcohol A wherein n is 2.

Alcohol A is used as described previously herein to form alcohol-ester VII wherein n is 2, which is treated with a silane protecting compound as described hereinbefore in the presence of an amine base (e.g., triethylamine) and an inert solvent (e.g., methylene chloride) and N,N-dimethylaminopyridine (DMAP) to form the protected alcohol

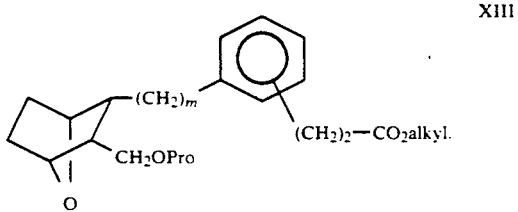

XIII

The protected alcohol XIII is then treated with lithium diisopropylamide in the form of a cooled (−78 to 0° C.) mixture of diisopropylamine and t-butyllithium or n-butyllithium under an inert atmosphere (e.g., argon). The resulting mixture is treated with diphenyl diselenide at about −78 to 25° C., to form the corresponding selenide

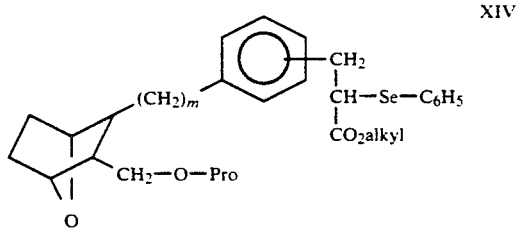

XIV

Selenide SIV in an inert organic solvent (e.g., ethyl acetate and/or methanol) is treated with an oxidizing agent (e.g., aqueous hydrogen peroxide) to form the cinnamate

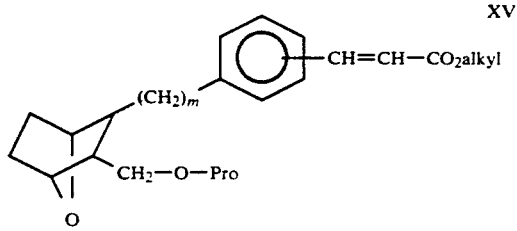

XV

The protecting group is removed from cinnamate XV by acetyl chloride in the presence of an organic solvent such as methanol to form the alcohol

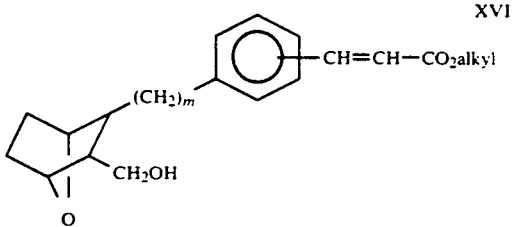

XVI which may then be employed to form compounds of formula I wherein Y is —CH=CH— following the procedures described for treatment of alcohol-ester VII.

Compounds of formula I wherein R is $CO_2R'$ and $R'$ is alkali metal can be prepared from the corresponding esters by treating the ester with bases such as lithium hydroxide or potassium hydroxide. The corresponding acids (wherein $R'$ is hydrogen) are prepared by neutralizing the foregoing alkali metal salts with an acid (e.g., dilute hydrochloric acid or oxalic acid).

Compounds of formula I wherein R is —$CH_2OH$ may be prepared by treating the corresponding esters (wherein R is $CO_2R'$ and $R'$ is alkyl) with a reducing agent such as $LiBH_4$ in the presence of diethyl ether and THF.

Compounds of the invention wherein R is $CONHSO_2R^3$ are prepared by treating the associated acids (wherein R is $CO_2H$) with a sulfonamide

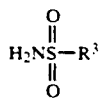

I in the presence of a coupling agent (e.g., carbonyldiimidazole or WSC) in the presence of an amine (e.g., dimethylaminopyridine) under an inert atmosphere (e.g., argon).

Compounds wherein R is —$CH_2$-5-tetrazolyl are prepared by reacting the associated ester with, in sequence, (1) a hydride reducing reagent (e.g., lithium borohydride or sodium borohydride), (2) triphenylphosphonium dibromide in an inert solvent such as toluene, (3) an alkali metal cyanide in a polar solvent such as methanol/water, and (4) sodium azide in the presence of ammonium chloride, DMF and lithium chloride at about 100 to 130° C.

Compounds of formula I wherein R is $CONHR^4$ wherein $R^4$ is other than hydrogen may be prepared from the corresponding acid by treatment with WSC in the presence of DMF, HOBT, an organic base (e.g., triethylamine) and an amine

HNHR⁴. J

Where $R^4$ is hydrogen, ammonium chloride is used in place of the above amine.

The compounds of this invention have four centers of asymmetry as indicated by the asterisks in formula I. However, it will be apparent that each of the formulae set out above which do not include asterisks still represent all of the possible stereoisomers thereof. All of the various stereoisomeric forms are within the scope of the invention.

The various stereoisomeric forms of the compounds of the invention, namely, cis-exo, cis-endo and all trans forms and stereoisomeric pairs may be prepared with starting materials and procedures in U.S. Pat. No. 4,143,054.

The nucleus in each of the compounds of the invention is depicted as

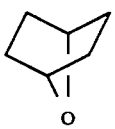

for convenience; the nucleus may also be depicted as

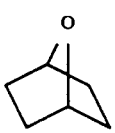

Use and Utility

The compounds of this invention are thromboxane receptor antagonists and as such are useful as inhibitors of thromboxane receptor mediated actions. The term "thromboxane receptor antagonist" includes compounds that are so-called thromboxane $A_2$ receptor antagonists, thromboxane $A_2$ antagonists, thromboxane $A_2$/prostaglandin endoperoxide antagonists, TP-receptor antagonists, or thromboxane antagonists.

The compounds of the invention are also thromboxane synthetase inhibitors and thus are useful as inhibitors of thromboxane production.

The compounds of this invention are useful as inhibitors of platelet function, i.e., for the prevention and treatment of thrombotic vascular occlusive disorders, whether complete or partial, for example, arterial thrombosis, including that of the coronary, cerebral, ophthalmic, hepatic, mesenteric, renal, peripheral arteries or vascular or organ grafts, unstable angina, transient ischemic attacks, or intermittent claudication. They may be useful to prevent thrombosis following vascular injury produced in the course of diagnostic or therapeutic procedures such as endarterectomy or angiography. The compounds may be useful in the treatment or prevention of disorders characterized by platelet consumption and/or activation, including platelet activation, dysfunction, and/or loss during extracorporeal circulation, the use of radiographic contrast agents, thrombotic thrombocytopenia purpura, disseminated intravascular coagulation, purpura fulminans, hemolytic transfusion reaction, or hemolytic uremic syndrome, systemic lupus, cyclosporine-induced renal toxicity, pulmonary hypertension, side effects from dialysis, or abdominal aortic aneurism repair. The compounds may be used in the treatment of venous thrombosis or embolism, including pulmonary embolism, deep venous thrombosis, hepatic vein thrombosis, and renal vein thrombosis.

The compounds of this invention are useful as inhibitors of arterial or venous vasoconstriction. Accordingly, they may be useful to prevent vasoconstriction associated with unstable angina, chronic stable angina, and variant, or Prinzmetal's angina, Raynaud's syndrome, migraine headache, vasospasm of the coronary, cerebral, ophthalmic, hepatic, mesenteric, renal, peripheral arteries or vascular grafts, vascular injury such as that associated with surgery or trauma. Hypertension of pregnancy, the hepato-renal syndrome, and pulmonary hypertension are additional examples of vasoconstrictive disorders treatable by the compounds of this invention.

The compounds of this invention are useful as inhibitors of bronchoconstriction, i.e., airway hyperresponsiveness, allergic bronchospasm, asthma, and bronchoconstrictive responses to environmental, infectious, noxious or mechanical stimuli.

The compounds of this invention are useful as inhibitors of ischemic and reperfusion injury to various tissues, including, myocardium, skin, brain, bowel, or kidney, alone or in combination with other agents intended to restor blood flow. For example, these compounds may be useful for improving postischemic myocardial function and decreasing myocardial infarct size. Ischemia caused by reduced blood flow during diagnostic or therapeutic procedures may benefit by treatment with these compounds, for example, they reduce the myocardial stunning observed after bypass surgery. In addition, they may be useful for reducing the tissue injury caused by a stroke.

The compounds of this invention may be useful in the prevention or treatment of other conditions including burns, diabetic retinopathy, tumor metastases and tardive dyskinesia. The compounds may be useful in potentiating diuretic-induced diuresis.

In addition, the thromboxane receptor antagonists of the invention may be used with a thrombolytic agent such as t-PA, streptokinase, urokinase, prourokinase or anisoylated plasminogen-streptokinase activator complex (APSAC) within 6 hours of a myocardial infarction. In such case, the thrombolytic agent may be used in amounts conventionally employed, for example, as disclosed in the Physicians' Desk Reference for reducing post-ischemic myocardial injury.

The compounds of the invention can be administered orally or parenterally to various mammalian species known to be subject to such maladies, e.g., humans, cats, dogs and the like in an effective amount within the dosage range of about 0.1 to about 100 mg/kg, preferably about 0.2 to about 50 mg/kg and more preferably about 0.5 to about 25 mg/kg (or from about 1 to about 2500 mg, preferably from about 5 to about 2000 mg) on a regimen in single or 2 to 4 divided daily doses.

The active substance can be utilized in a composition such as tablet, capsule, solution or suspension containing about 5 to about 500 mg per unit of dosage of a compound or mixture of compounds of formula I or in topical form for wound healing (0.01 to 5% by weight compound of formula I, 1 to 5 treatments per day). They may be compounded in conventional matter with a physiologically acceptable vehicle or carrier, excipient, binder, preservative, stabilizer, flavor, etc., or with a topical carrier such as Plastibase (mineral oil gelled with polyethylene) as called for by accepted pharmaceutical practice. Also as indicated in the discussion above, certain members additionally serve as intermediates for other members of the group.

The compounds of the invention may also be administered topically to treat peripheral vascular diseases and as such may be formulated as a cream or ointment.

PREFERRED EMBODIMENTS

The following Examples represent preferred embodiments of the present invention. Unless otherwise indicated, all temperatures are expressed in degrees Celsius.

EXAMPLE 1

[1S-(1α, 2α, 3α, 4α)]-2-[[3-[[[2-[(4-Cyclohexylbutyl)-amino]-2-oxoethyl]amino]carbonyl]-7-oxabicyclo[2.2.1]hept-2-yl]methyl]-benzenepropanoic acid, methyl ester

A. 3-(2-Bromophenyl)-2-propenoic acid, methyl ester

To a stirred solution of 161.2 g (871 mmol) of 2-bromobenzaldehyde in 700 mL of dry THF (distilled from potassium/benzophenone) at room temperature under argon, was added 298.4 g (892 mmol, 1.024 equiv) of methyl(triphenylphosphoranylidene)acetate (Aldrich) over 1 hour in 20 g portions. Reaction was mildly exothermic and the mixture became homogeneous. The resulting solution was stirred for 18 hours during which some precipitate formed. Addition of 200 mL hexane caused further precipitation. Filtration was followed by evaporation. The residue was slurried with a large volume of hexane (more precipitation) and refrigerated overnight. This was filtered, and the filtrate was passed through a plug of silica gel (approximately 1 kg), eluting with 10% ethyl acetate (EtOAc) in hexane. The eluant was concentrated in vacuo to give 201.5 g of a colorless oil. This oil was pure title compound as a 4:1 mixture of double bond isomers (trans predominating). The yield of title compound was 96%.

B. 2-Bromobenzenepropanoic acid, methyl ester

A mixture of 201.5 g (836 mmol) of the Part A acrylate and 8.4 g of 5% rhodium on alumina catalyst (MCB) in 1.0 L of methanol was stirred at room temperature under an atmosphere of hydrogen (balloon) for over 8 hours. $^1$H NMR analysis of an aliquot showed about a 1:1 mixture of title compound and trans Part A compound with no cis Part A compound. The mixture was diluted with 500 mL additional methanol (MeOH) and 12.6 g more catalyst was added. After hydrogenation overnight, the reaction was complete. The reaction mixture was passed through Celite and a Millipore/Fluropore membrane filter (0.5 μm FH) with a prefilter pad, and the filtrate was concentrated in vacuo to obtain two immiscible oils. One of the oils was water-soluble and gave a highly acid aqueous solution. Solid NaHCO$_3$ and Na$_2$SO$_4$ were carefully added (gas was evolved). The mixture was diluted with CH$_2$Cl$_2$, filtered, and evaporated (and re-evaporated with CH$_2$Cl$_2$ to drive off methanol) to obtain 196.9 g of clear oil. This oil was 95% pure title compound with 5% of debromo title compound. The corrected yield of the title compound was 92% (187.1 g).

C. 2-Bromobenzenepropanol

To a stirring solution of 196.9 g (95% pure=187.1 g, 770 mmol) of compound B in 770 mL of toluene under argon cooled to 0° C. (ice bath), 830 mL of 1.0 M diisobutylaluminum hydride (DIBAL-H) in toluene solution (830 mmol, Aldrich) was added over 45 minutes. The reaction was not very exothermic. After the mixture was stirred for 1 hour, TLC indicated approximately half of the starting material remained. Next, 580 mL of 1.5 M DIBAL-H in toluene solution (870 mmol, Aldrich) was added slowly. The ice bath was removed and stirring was continued for 2 hours. The mixture was then poured slowly into 1.2 L of 6 M aqueous HCl stirring in an ice bath. This quench was exothermic and gas was evolved. After the mixture was recooled to 0°, the layers were separated, and the organic layer was washed with 1 M aqueous HCl and brine. It was then dried over Na₂SO₄ and MgSO₄ and evaporated (and re-evaporated with CH₂Cl₂ to drive off toluene) to obtain 173.0 g of clear, colorless oil. This oil was 95% pure title compound with 5% of debromo title compound. The corrected yield of the title compound was 99% (164.3 g).

D. 1-Bromo-2-[3-[[Dimethyl(1,1,2-trimethylpropyl)silyl]oxy]propyl]benzene

To a solution of 29.0 g (135 mmol) of the crude Part C alcohol and 24.1 g (135 mmol, Petrarch) of thexyldimethylchlorosilane in 200 mL of dry methylene chloride (distilled from phosphorous pentoxide) was added at room temperature 20 mL (143 mmol, distilled from calcium hydride) of triethylamine and then 200 mg (1.64 mmol, Aldrich) of 4-dimethylaminopyridine. The reaction mixture was stirred at room temperature for 18 hours. The resulting slurry was diluted with 100 mL of hexane, cooled to 0° C. with stirring for 15 minutes, then filtered to remove solid triethylamine hydrochloride. The filtrate was concentrated in vacuo to give an oil. The crude oil was purified by flash chromatography (Merck silica, 15×10 cm, 1:9 ethyl acetate/petroleum ether) to afford 45.5 g (127 mmol, 94%) of the title compound as a colorless liquid.

E. [1S-(1α, 2α, 3α, 4α)]-[2-[3-[[Dimethyl(1,1,2-trimethylpropyl)silyl]oxy]propyl]phenyl]-7-oxabicyclo[2.2.1]heptane-2,3-dimethanol To a solution of 5.00 g (14.0 mmol) of compound D in 30 mL of dry diethyl ether (distilled from ketyl) cooled to −100° C. was added dropwise 15 mL (1.7 M in pentane, 25 mmol, Aldrich) of t-butyllithium solution over 15 minutes. The reaction mixture was stirred at −100° C. for 15 minutes then at 0° C. for 15 minutes. The resulting pale yellow anion solution was recooled to −78° C., 30 mL of dry THF (distilled from ketyl) was introduced, and a solution of 875 mg (5.61 mmol) of [3aR-(3aα,4β, 7β, 7aα)]-octahydro-4,7-epoxyisobenzofuran-1-ol in 10 mL of THF was rapidly added. The reaction mixture was warmed to 0° C., stirred for 1 hour, quenched with 5 mL of water, then partitioned between 100 mL of water and 25 mL of ethyl acetate. The organic layer was separated and the aqueous layer was extracted with an additional 25 mL of ethyl acetate. The organic extracts were combined, dried (magnesium sulfate), and concentrated in vacuo to give an oil. The crude oil was purified by flash chromatography (Merck silica, 12×5.0 cm, 1:4 ethyl acetate/petroleum ether then 4:1 ethyl acetate/petroleum ether) to afford 2.35 g (5.41 mmol, 97%) of the title diasteromeric alcohols as a colorless oil.

F. [1S-(1α, 2α, 3α, 4α)]-2-[[2-[3-[[Dimethyl(1,1,2-trimethylpropyl)silyl]oxy]propyl]-phenyl]methyl]-7-oxabicyclo[2.2.1]heptane-3-methanol A mixture of 1.90 g (4.38 mmol) of the Part E diastereomeric alcohols and 1.9 g of 20% palladium hydroxide on carbon catalyst (moist, less than 50% water, Aldrich) in 60 mL of glacial acetic acid was stirred rapidly under an atmosphere of hydrogen (balloon) for 5 hours. The reaction mixture was filtered through a 0.4 μM polycarbonate membrane and the filtrate was concentrated in vacuo (room temperature bath). The residue was partitioned between 50 mL of water and 50 mL of ethyl acetate. The organic layer was separated, washed with 50 mL of 1 M aqueous sodium hydroxide solution, dried (magnesium sulfate), and concentrated in vacuo to give an oil. The crude material was purified by flash chromatography (Merck silica, 12×5.0 cm, 1:2 ethyl acetate/ petroleum ether) to afford 1.03 g (2.39 mmol, 55%) of the title compound as a colorless oil. In addition, 573 mg (1.37 mmol, 30%) of the Part E starting material (as a single diastereomer) was recovered.

G. [1S-(1α, 2α, 3α, 4α)]-2-[[3-(Hydroxymethyl)-7-oxabicyclo[2.2.1]hept-2-yl]methyl]benzenepropanoic acid, methyl ester A solution of 1.00 g (2.39 mmol) of compound F and 50 mg (0.41 mmol, Aldrich) of 4-dimethylaminopyridine in 6 mL of 1:1 dry pyridine/acetic anhydride was stirred at room temperature for 2 hours. The reaction mixture was concentrated in vacuo and the residue partitioned between 25 mL of ethyl acetate and 20 mL of 1 M aqueous HCl solution. The organic layer was separated, washed with 20 mL of 1 M aqueous NaOH and 20 mL of brine, dried (magnesium sulfate), and concentrated in vacuo to afford the crude acetate as an oil.

To a solution of the crude acetate in 15 mL of reagent acetone cooled to 0° was added rapidly 3.3 mL of Jones reagent (2.6 M in Cr⁺⁶, see Fieser & Fieser, *Reagents for Organic Synthesis*, Vol. 1, p. 142). The reaction mixture was stirred for 2 hours, quenched by addition of 1 mL of isopropanol and stirred for an additional 30 minutes. The resulting green slurry was filtered through a pad of Celite. The filtrate was concentrated in vacuo and the residue partitioned between 25 mL of diethyl ether and 25 mL of water. The organic layer was separated and concentrated in vacuo to give the crude acetate-acid as an oil.

A solution of the crude acetate-acid in 15 mL of 2:1 1 M aqueous NaOH/THF was stirred at room temperature for 30 minutes. The reaction mixture was cooled in an ice-bath, quenched by 15 mL of 1 M aqueous HCl solution, then extracted with two 25-mL portions of diethyl ether. The ether extracts were combined, washed with 25 mL of brine and concentrated in vacuo to give the crude alcohol-acid as an oil.

A solution of the crude alcohol-acid in 10 mL of acidic methanol (prepared by addition of 0.5 mL of acetyl chloride to 10 mL of dry methanol at 0° C.) was stirred at 0° for 2 hours and then concentrated in vacuo. The resulting oil was purified by flash chromatography (Merck silica, 15 ×3.0 cm, ethyl acetate) to afford 526 mg (1.76 mmol, 74% from compound F) of the title compound as a colorless oil.

H. [1S-(1α, 2α, 3α, 4α)]-2-[[3-CArboxy-7-oxabicyclo[2.2.1]hept-2-yl]methyl]benzenepropanoic acid, methyl ester To a solution of 495 mg (1.63 mmol) of compound G in 5 mL of reagent acetone cooled to 0° C. was added rapidly 2.0 mL (2.6 M in Cr⁺⁶) of Jones reagent. The reaction mixture was warmed to room temperature, stirred for 2 hours, then quenched by about 1 mL of isopropanol. After 15 minutes, the resulting green slurry was filtered through a pad of Celite. The filtrate was partitioned between 20 mL of dietyl ether and 20 mL of water. The organic layer was separated, and the aqueous layer was extracted with an additional 20 mL of diethyl ether. The ether extracts were combined, dried (magnesium sulfate), and concentrated in vacuo to give 560 mg (1.59 mmol, 98%) of crude title compound as a colorless oil.

I. N-(4-Cyclohexylbutyl)-2-aminoacetamide, monohydrochloride

To a stirred solution of 1.14 g (.65 mmol) of t-butyloxycarbonyl-glycine in 10 mL of tetrahydrofuran at 0° C. was added 1.05 g (6.5 mmol) of carbonyldiimidazole. The ice bath was removed and the reaction mixture was allowed to warm to room temperature over a period of 90 minutes. To this mixture was added 1.18 g (6.14 mmol) of 4-cyclohexylbutylamine hydrochloride followed by 1.0 mL of triethylamine (7.2 mmol). An exotherm was noted which was accompanied by the formation of a thick precipitate. An additional 5.0 mL of tetrahydrofuran was added and the reaction mixture was allowed to stir at room temperature for 18.5 hours. The reaction mixture was diluted with 30 mL of water, acidified to pH 4 with 1 N hydrochloric acid, and extracted with two 30 mL portions of ethyl acetate. The combined ethyl acetate extracts were washed with 30 mL of 0.1 N sodium hydroxide, dried (magnesium sulfate), filtered and concentrated in vacuo to afford 1.97 g of crude amide. To a flask containing the above amide was added 20 mL of pre-chilled (0° C.) trifluoroacetic acid. After stirring at 0° C. for 30 minutes, the reaction mixture was concentrated in vacuo at 0° C. The residue was reconcentrated from 25 mL of toluene. The residue was dissolved in 25 mL of methanol and treated with approximately 1 mL of concentrated hydrochloric acid. This was concentrated in vacuo, redissolved in methanol, and reconcentrated to afford a viscous oil. This was triturated in 50 mL of ether to afford 1.38 g of the title compound (84% overall).

J. [1S-(1α, 2α, 3α, 4α)]-2-[[3-[[[2-[(4-Cyclohexylbutyl)amino]-2-oxoethyl]amino]-carbonyl]-7-oxabicyclo[2.2.1]hept-2-yl]methyl]benzenepropanoic acid, methyl ester To a solution of 280 mg (0.88 mmol) of acid H in 10 mL sieve-dried dimethylformamide, stirring at 0°, were added 207 mg (0.88 mmol) of amine hydrochloride I, 149 mg (0.88 mmol, Aldrich) hydroxybenztriazole hydrate and 0.37 mL (2.64 mmol, distilled from calcium hydride) triethylamine. The reaction mixture was stirred at room temperature for 16 hours, concentrated in vacuo, then dissolved in 100 mL ethyl acetate and washed with 2×20 mL 1 M hydrochloric acid, 2×10 mL 0.2 M sodium hydroxide and 1×15 mL saturated sodium hydrogen carbonate. The ethyl acetate layer was dried (magnesium sulfate) and concentrated in vacuo to give a crude solid. The crude solid was flash-chromatographed (Merck silica, 2:1 ethyl acetate:hexane, then ethyl acetate) to give an impure solid; this solid was recrystallized from hot hexane/ethyl acetate to give 232 mg (0.45 mmol, 58%) of ester J as a white solid.

EXAMPLE 2

[1S-(1α, 2α, 3α, 4α)]-2-[[3-[[[2-[(4-Cyclohexylbutyl)amino]-2-oxoethyl]maino]carbonyl]-7-oxabicyclo-[2.2.1]hept-2-yl]methyl]-benzenepropanoic acid To a solution of 232 mg (0.45 mmol) of ester Example 1 (distilled from K, benzophenone) in 8 mL tetrahydrofuran/2 mL water was added 38 mg (0.91 mmol, Aldrich) of lithium hydroxide monohydrate. The reaction was stirred vigorously at room temperature for 3 hours, then quenched by the addition of 1.81 mL (1.8 mmol) 1 M hydrochloric acid solution. The mixture was partitioned between 30 mL water and 30 mL ethyl acetate; the ethyl acetate layer was separated, dried (magnesium sulfate), and concentrated in vacuo to give 210 mg (0.42 mmol, 93%) of acid Example 2 as a white foam, melting point 152–155°. TLC: $R_f$ (silica gel, 1:9 methanol:methylene chloride)=0.18, ammonium molybdate/ceric sulfate and UV, homogeneous.

Analysis for $C_{29}H_{42}N_2O_5$:
Calc'd: C,69.85; H,8.49; N,5.62
Found: C,69.79; H,8.70; N,5.59.

EXAMPLE 3

[1S-(1α, 2α, 3α, 4α)]-[2-[[3-[[[(4-Cyclohexylbutyl)amino]2oxoethyl]amino]carbonyl]-7-oxabicyclo[2.2.1]-hept-2-yl]methyl]phenoxy]acetic acid, ethyl ester

A. 1-Bromo-2-(methoxymethoxy)benzene

The oil was removed from 4.5 g (60% in oil, 112 mmol, Aldrich) of sodium hydride dispersion by three 20-mL washes with hexane then the residue was covered with 75 mL of dimethylformamide (Burdick and Jackson). The resulting mixture was heated to about 50° and 18.1 g (105 mmol, Aldrich) of 2-bromophenol was added dropwise over 15 minutes. Vigorous gas evolution was observed. The reaction was stirred for an additional 30 minutes, and the resulting gray-brown solution was cooled to 0°. Bromomethyl methyl ether (9.6 mL, 117 mmol, Aldrich) was added dropwise over 15 minutes. The reaction mixture was stirred for 1 hour at 0°, then at room temperature for 16 hours. The resulting slurry was partitioned between 200 mL of 1 M aqueous sodium hydroxide solution and 150 mL of 4:1 hexane/diethyl ether. The aqueous layer was separated and extracted with an additional 100 mL of 4:1 hexane/diethyl ether. The organic extracts were combined, washed with two 200-mL portions of water, dried (magnesium sulfate) and concentrated in vacuo to give 22.2 g (102 mmol, 97%) of title compound as a pale yellow liquid.

B. [1S-(1α, 2α, 3α, 4α)]-[2-(Methoxymethoxy)phenyl]-7-oxabicyclo[2.2.1]heptane -2,3-dimethanol To a solution of 16.7 g (77.0 mmol) of Part A aryl bromide in 150 mL of dry THF (distilled from potassium/benzophenone) cooled to −78° was added dropwise 48 mL (1.6 M in hexane, 77 mmol, Aldrich) of n-butyllithium over 30 minutes. The reaction mixture was stirred at −78° for 1 hour. To the resulting white slurry of the anion was added a solution of 4.80 g (30.8 mmol, of [3aR-(3aα,4β, 7β, 7aβ)]-octahydro-4,7-epoxyisobenzofuran-1-ol in 30 mL of dry THF over 5 minutes. The reaction was warmed to 0° (becomes homogeneous), stirred for 2 hours then quenched with 5 mL of methanol and concentrated in vacuo. The residue was partitioned between 100 mL of brine and 100 mL of ethyl acetate, and then an additional 50 mL of water was added. The aqueous layer was separated and extracted with 100 mL of ethyl acetate. The organic extracts were combined, dried (magnesium sulfate) and concentrated in vacuo to give an oil. The crude material was purified by flash chromatography (Merck silica, 22×5.0 cm, 1:2 ethyl acetate/petroleum ether then ethyl acetate) to afford 8.49 g (28.9 mmol, 94%) of the title diol as an oil.

C. [1S-(1α, 2α, 3α, 4α)]-2-[[2-(Methoxymethoxy)phenyl]methyl]-7-oxabicyclo-2.2.1]heptane-3-methanol A mixture of 8.40 g (28.6 mmol) of Part B diol and 8.0 g of 10% palladium on carbon catalyst (Aldrich) in 75 mL of glacial acetic acid was stirred under an atmosphere of hydrogen (balloon) for 18 hours. The resulting mixture was filtered on a Buchner funnel then passed through a polycarbonate membrane. The filtrate was concentrated in vacuo (oil pump vacuum) to give an oil. The oil was partitioned between 75 mL of ethyl acetate and 100 mL of 1 M aqueous sodium hydroxide solution (pH=12 of aqueous) then an equal volume of brine was added (100 mL). The aqueous layer was separated and extracted with an additional 50 mL of ethyl acetate. The organic extracts were combined, dried (magnesium sulfate) and concentrated in vacuo to afford 7.56 g (27.2 mmol, 95%) of title alcohol as a colorless oil.

D. [1S-(1α, 2α, 3α, 4α)]-2-[[2-(Methoxymethoxy)phenyl]methyl]-3-[(phenylmethoxy) methyl]-7oxabicyclo[2.2.1]heptane The oil was removed from 552 mg (60% in oil, 13.8 mmol, Aldrich) of sodium hydride dispersion by three washes with petroleum ether. The residue was then covered with 15 mL of dry THF (distilled from potassium/benzophenone). The mixture was heated to about 50°, and then a solution of 3.50 g (12.6 mmol) of Part C alcohol in 15 mL of dry THF was added dropwise. Vigorous gas evolution was observed. The reaction was stirred for an additional 30 minutes, then cooled to 0°. To the resulting anion solution was added 465 mg (1.26 mmol, Fluka) of tetra-n-butylammonium iodide then dropwise 1.6 mL (14 mmol, Aldrich) of benzyl bromide. The reaction was stirred at 0° for 2 hours then at room temperature for 16 hours. The resulting mixture was quenched with 5 mL of water and then partitioned between 100 mL of 1 M aqueous HCl solution and 50 mL of ethyl acetate. The aqueous layer was separated and extracted with an additional 50 mL of ethyl acetate. The organic extracts were combined, washed with 100 mL of 1 M aqueous sodium hydroxide solution, dried (magnesium sulfate) and concentrated in vacuo to give 4.55 g (12.4 mmol, 98%) of crude title compound as a yellow oil.

E. [1S-(1α, 2α, 3α, 4α)]-2-[[3-[(Phenylmethoxy)methyl]-7-oxabicyclo[2.2.1]hept-2yl]methyl]phenol To a solution of 4.53 g (12.3 mmol) of Part D title compound in 12 mL of dioxane (Burdick and Jackson) was added at room temperature 30 mL of 1:4 concentrated HCl/methanol. The reaction was stirred for 5 hours and then concentrated in vacuo. The residue was partitioned between 50 mL of 1 M aqueous HCl solution and 75 mL of ethyl acetate, and then 50 mL of brine was added. The organic layer was separated, dried (magnesium sulfate) and concentrated in vacuo to give an orange oil. The crude oil was purified by flash chromatography (Merck silica, 12×5.0 cm, 1:1:3 ethyl acetate/ methylene chloride/hexane) to afford 3.46 g (10.7 mmol, 87%) of title phenol as a pale yellow glass.

F. [1S-(1α, 2α, 3α, 4α)]-2-[[3-[(Phenylmethoxy)methyl]-7-oxabicyclo2.2.1]hept-2-yl]methyl]phenoxy]acetic acid, ethyl ester The oil was removed from 420 mg (60% in oil, 11 mmol, Aldrich) of sodium hydride dispersion by three washes with hexane, and then 15 mL of dry THF (distilled from potassium/benzophenone) was added. To the resulting stirred mixture at room temperature was added dropwise a solution of 3.30 g (10.2 mmol) of Part E phenol in 20 mL of dry THF over about 15 minutes. Vigorous gas evolution was observed. The reaction was stirred for an additional 30 minutes, cooled to 0°, and a solution of 1.75 g (10.5 mmol, Aldrich) of ethyl bromoacetate in 2 mL of THF was added dropwise. The reaction mixture was stirred for 1.5 hours then quenched with 50 mL of 1 M aqueous HCl solution. The resulting mixture was added to 50 mL of brine then extracted with 75 mL of ethyl acetate. The organic extract was dried (magnesium sulfate) and concentrated in vacuo to give an oil. The crude oil was purified by flash chromatography (Merck silica, 12×5.0 cm, 1:2 ethyl acetate/hexane) to afford 3.87 g (9.44 mmol, 93%) of title ester as a pale yellow oil.

G. [1S-(1α, 2α, 3α, 4≠)]-[2-[[3-(Hydroxymethyl)-7-oxabicyclo[2.2.1]hept-2-yl]methyl]phenoxy]acetic acid, ethyl ester A mixture of 3.60 g (8.78 mmol) Part F ester and 180 mg of 20% palladium hydroxide on carbon catalyst (moist, Aldrich) in 25 mL of ethyl acetate was stirred under hydrogen (balloon) for 2 hours (TLC showed little reaction). Added to the reaction was 12 mL of absolute ethanol and then 0.3 ml of concentrated HCl. The reaction was stirred for 2 hours (TLC showed little reaction) and then an additional 360 mg of catalyst was added. The resulting mixture was stirred for 20 hours, filtered on a Buchner funnel and through a polycarbonate membrane. The filtrate was concentrated in vacuo to give an oil. The crude oil was purified by flash chromatography (Merck silica, 15×5.0 cm, 2:1 ethyl acetate/hexane) to afford 1.20 g (3.75 mmol, 43%) of desired title alcohol as an oil and 1.48 g (4.09 mmol, 47%) of corresponding acetate as an oil.

H. [1S-(1α, 2α, 3α, 4α)]-[2-[[3-Carboxy-7-oxabicyclo[2.2.1]hept-2-yl]methyl]phenoxy]acetic acid, ethyl ester To a solution of 1.17 g (3.66 mmol) of Part G alcohol in 15 mL of reagent acetone cooled to 0° was added rapidly 2.5 mL (2.6 M in $Cr^{+6}$, 6.5 mmol) of Jones reagent. The reaction was stirred for 1 hour at 0°, then 30 minutes at room temperature. The mixture was re-cooled to 0°, quenched with 2 mL of isopropanol and stirred for an additional 30 minutes. The resulting green slurry was filtered through a pad of Celite. The filtrate was concentrated in vacuo and the residue partitioned between 20 mL of 1 M HCl solution and 20 mL of ethyl acetate. The organic extract was separated, washed with 20 mL of brine, dried (magnesium sulfate) and concentrated in vacuo to give 1.19 g (3.56 mmol, 97%) of crude title acid as an oil.

1. [1S-(1α, 2α, 3α, 4α)]-[2-[3-[[[[(4-Cyclohexylbutyl)amino]2-oxoethyl]amino]carbonyl]-7-oxabicyclo[2.2.1]hept-2-yl]methyl]-phenoxy]acetic acid, ethyl ester To a solution of 200 mg (0.60 mmol) of compound H in 5 mL of dry tetrahydrofuran (distilled from K/benzophenone) cooled to 0° was added 90 mg (0.67 mmol, Aldrich) of 1-hydroxybenzotriazole hydrate, 166 mg (0.67 mmol) of amine hydrochloride I from Example 1 and 200 μL (1.4 mmol, distilled from calcium hydride) of triethylamine. The reaction mixture was stirred for several minutes, and then 137 mg (0.67 mmol, Aldrich) of 1,3-dicyclohexylcarbodiimide was introduced in one portion. The solution was stirred at 0° for 2 hours, after which 5 mL of dimethylformamide (Burdick and Jackson) was added and the reaction was stirred at room temperature for 16 hours. The resulting slurry was filtered and the filtrate concentrated in vacuo to remove dimethylformamide. The residue was partitioned between 20 mL of 1 M aqueous hydrochloric acid solution and 20 mL of ethyl acetate. The organic layer was separated, dried (magnesium sulfate) and concentrated in vacuo to give an oil. The crude material was purified by flash chromatography (Merck silica, 12×3.0 cm, 1:30 methanol/methylene chloride) and then recrystallized (ethyl acetate/hexane) to afford 185 mg (0.35 mmol, 58%) of ester Example 3 as white crystals, melting point 101–103°.

EXAMPLE 4

[1S-(1α, 2α, 3α, 4α)]-[2-[[3-[[[[(4-Cyclohexylbutyl)amino]2oxoethyl]amino]carbonyl]-7-oxabicyclo[2.2.1]hept-2-yl]methyl]-phenoxy]acetic acid To a solution of 180 mg (0.34 mmol) of ester Example 3 and 28 mg (0.67 mmol, Aldrich) of lithium hydroxide monohydrate in 5 mL of 4:1 tetrahydrofuran/water was stirred at room temperature for 2 hours. The reaction mixture was acidified by addition of 1.4 mL of 1 M aqueous hydrochloric acid solution and then partitioned between 15 mL of water and 20 mL of ethyl acetate. The organic layer was separated after addition of 15 mL of brine, washed with 20 mL of brine, dried (magnesium sulfate) and concentrated in vacuo to give a solid. The crude solid was recrystallized (acetonitrile) to yield 142 mg (0.28 mmol, 84%) of acid Example 4 as white crystals, melting point 173–174°.

TLC: $R_f$ (silica gel, 1:10:90 acetic acid/methanol/methylene chloride)=0.33, ammonium molybdate/ceric sulfate and UV, homogeneous.

Analysis for $C_{28}H_{40}N_2O_6$:
Calc'd: C,67.17; H,8.05; N,5.60.
Found: C,67.31; H,8.26; N,5.56.

What is claimed is:
1. A compound having the formula

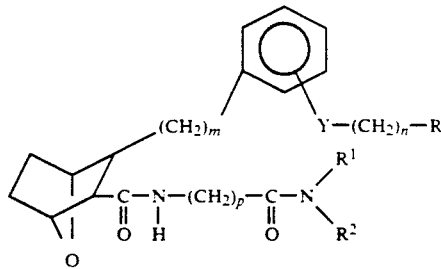

and all stereoisomers and pharmaceutically acceptable salts thereof, wherein:
m is 1, 2, or 3;
n is 1, 2 or 3, except that n is O when Y is vinylene;
p is 1, 2 or b 3;
R is $CO_2R'$, $CH_2OH$, $CONHSO_2R^3$, $CONHR^4$, or $-CH_2-$5-tetrazolyl;
R' is hydrogen, alkyl, or alkali metal;
Y is $-O-$, a single bond or vinylene;
$R^1$ is hydrogen, alkyl, alkenyl, alkynyl, aralkyl, aryl, cycloalkyl, cycloalkylalkyl, cycloheteroalkyl, cycloheteroalkylalkyl, heteroaryl or heteroarylalkyl, or

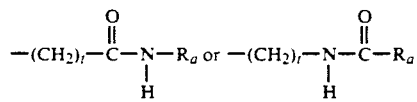

wherein t is 1 to 12 and $R_a$ is alkyl, aryl, cycloalkyl, or cycloalkylalkyl, each of $R^1$ being unsubstituted or optionally substituted with alkyl, aryl, cycloalkyl, or cycloalkylalkyl;
$R^2$ is hydrogen, alkyl, aryl, or aralkyl; or
$R^1$ and $R^2$, together with the nitrogen atom to which they are linked, form a 5- to 8-membered ring;
$R^3$ is alkyl, aryl or aralkyl; and
$R^4$ is hydrogen, alkyl, aryl or aralkyl.

2. The compound of claim 1 having the formula

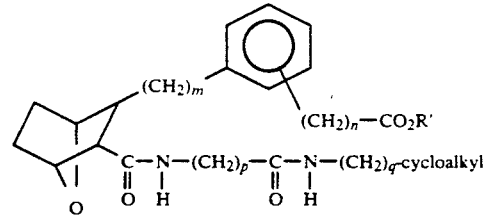

wherein q is an integer from 1 to 7.
3. The compound of claim 1, wherein m is 1.
4. The compound of claim 2, wherein m is 1.
5. The compound of claim 2, wherein q is 4.
6. The compound of claim 1, wherein n is 2.
7. The compound of claim 2, wherein n is 2.
8. The compound of claim 1, wherein R is $CO_2R'$.
9. The compound of claim 2, wherein R' is hydrogen.
10. The compound of claim 8, wherein R' is hydrogen.
11. The compound of claim 2, wherein the cycloalkyl group is cyclohexane.
12. The compound of claim 1, having the names:
[1S-(1α, 2α, 3α, 4α)]-2-[[3-[[2-[(4-cyclohexylbutyl)amino]-2-oxoethyl]amino]carbonyl]-7-oxabicyclo2.2.1]hept-2-yl]methyl]benzenepropanoic acid, methyl ester;

[1S-(1α, 2α, 3α, 4α)]-2-[[3-[[[2-[(4-cyclohexylbutyl)amino]-2-oxoethyl]amino]carbonyl]-7-oxabicyclo[2.2.1]hept-2-yl]methyl]benzenepropanoic acid;

[1S-(1α, 2α, 3α, 4α)]-[2-[[3-[[[(4-cyclobexylbutyl)amino]2-oxoethyl]amino]carbonyl]-7-oxabicyclo[2.2.1]hept-2-yl]methyl]phenoxy]acetic acid, ethyl ester; and

[1S-(1α, 2α, 3α, 4α)]-[2-[[3-[[[(4-cyclohexylbutyl)amino]2-oxoethyl]amino]carbonyl]-7-oxabicyclo[2.2.1]hept-2-yl]methyl]phenoxy]acetic acid.

13. A method of inhibiting platelet aggregation and bronchoconstriction, which comprises administering to the circulatory system of a mammalian host an effective amount of a compound as defined in claim 1.

14. The method as defined in claim 13 wherein said compound is administered in an amount within the range of from about 0.1 to about 100 mg/kg.

15. A composition for inhibiting platelet aggregation and bronchoconstriction comprising an effective amount of a compound as defined in claim 1 and a pharmaceutically acceptable carrier therefor.

16. A method of inhibiting platelet aggregation which comprises administering to a mammalian host an effective amount of a compound as defined in claim 1.

17. A method of inhibiting bronchoconstriction associated with asthma, which comprises administering to a mammalian host an effective amount of a compound as defined in claim 1.

18. A method for improving post-ischemic myocardial function, which comprises administering to a mammalian host in need of such treatment an effective amount of a compound as defined in claim 1.

19. A method for treating toxemia during pregnancy, which comprises administering to a mammalian host in need of such treatment an effective amount of a compound as defined in claim 1.

20. A method for preventing or reducing venous thrombosis, which comprises administering to a mammalian host in need of such treatment an effective amount of a compound as defined in claim 1.

21. A method for preventing or reducing platelet loss during extracorporeal circulation, which comprises administering to a mammalian host in need of such treatment an effective amount of a compound as defined in claim 1.

22. A method for treating burn injuries and/or promoting wound healing, which comprises administering to a mammalian host in need of such treatment an effective amount of a compound as defined in claim 1 in systemic or topical form.

23. A method for reducing post-ischemic myocardial injury, which comprises administering to a mammalian host in need of such treatment an effective amount of a compound as defined in claim 1 and an effective amount of a thrombolytic agent within 6 hours of a myocardial infarction.

24. The method as defined in claim 23 wherein said thrombolytic agent is t-PA, streptokinase, urokinase, prourokinase or anisoylated plasminogen-streptokinase activator complex.

* * * * *